US008529847B2

(12) United States Patent
Arras et al.

(10) Patent No.: US 8,529,847 B2
(45) Date of Patent: Sep. 10, 2013

(54) REAGENT KIT FOR ANALYZING APPARATUS

(75) Inventors: Georg Werner Arras, Reichelsheim (DE); Reinhold Kraemer, Peissenberg (DE); Klaus Oswald, Riedstadt (DE); Stephan Sattler, Starnberg (DE); Gottfried Senftner, Lampertheim (DE); Markus Winkenbach, Bürstadt (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/397,751

(22) Filed: Feb. 16, 2012

(65) Prior Publication Data
US 2012/0195808 A1 Aug. 2, 2012

Related U.S. Application Data

(63) Continuation of application No. PCT/EP2010/062116, filed on Aug. 19, 2010.

(30) Foreign Application Priority Data

Aug. 19, 2009 (EP) .................................... 09168175

(51) Int. Cl.
*B65D 43/08* (2006.01)
*B65D 43/16* (2006.01)
(52) U.S. Cl.
USPC ........ 422/430; 422/501; 215/237; 435/304.1; 435/305.3; 220/23.4; 220/502
(58) Field of Classification Search
USPC .............. 422/430, 501; 215/237; 435/304.1, 435/305.3; 220/23.4, 502
See application file for complete search history.

(56) References Cited

U.S. PATENT DOCUMENTS

| 5,246,665 | A | 9/1993 | Tyranski et al. |
| 5,862,934 | A | 1/1999 | Sattler et al. |
| 6,190,617 | B1 | 2/2001 | Clark et al. |
| 2001/0013169 | A1 | 8/2001 | Fassbind et al. |
| 2001/0028863 | A1 | 10/2001 | Kitagawa |
| 2003/0044323 | A1 | 3/2003 | Diamond et al. |

FOREIGN PATENT DOCUMENTS

| EP | 0523425 A1 | 1/1993 |
| EP | 0703457 A2 | 3/1996 |
| EP | 1923705 A1 | 5/2008 |
| JP | 10-311835 A | 11/1998 |

OTHER PUBLICATIONS

International Search Report issued Jan. 14, 2011 in PCT Application No. PCT/EP2010/062116.

*Primary Examiner* — Lyle Alexander
(74) *Attorney, Agent, or Firm* — Roche Diagnostics Operations, Inc.

(57) ABSTRACT

A reagent kit is provided comprising a plurality of containers with top-side openings, a common support structure or a plurality of support structures associated to the containers, and a plurality of caps. Each container and cap is mountable or provided on the common or the associated support structure, wherein each cap is formed essentially rectangular, having two shorter edges and two longer edges, and comprises: a cap body, a lid hinged to the cap body so to pivot around a pivot axis at least between closed and opened positions, the pivot axis being essentially parallel to the shorter edges. The containers and associated caps are arranged in a row along a connecting line such that the pivot axes are orthogonal to the connecting line. For at least one of the containers, an end portion of the cap body opposite to the pivot axis is not covered by the lid.

16 Claims, 13 Drawing Sheets

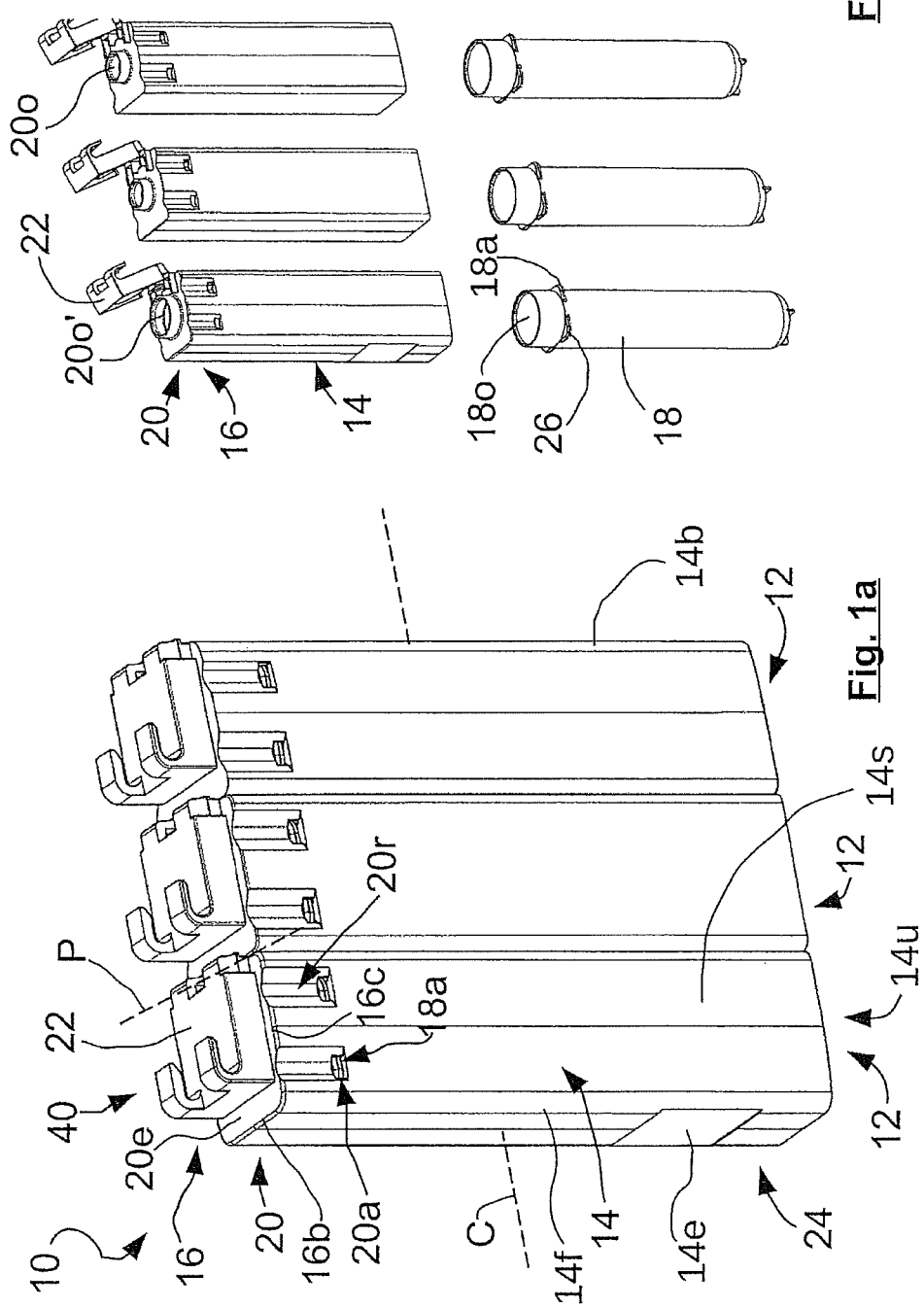

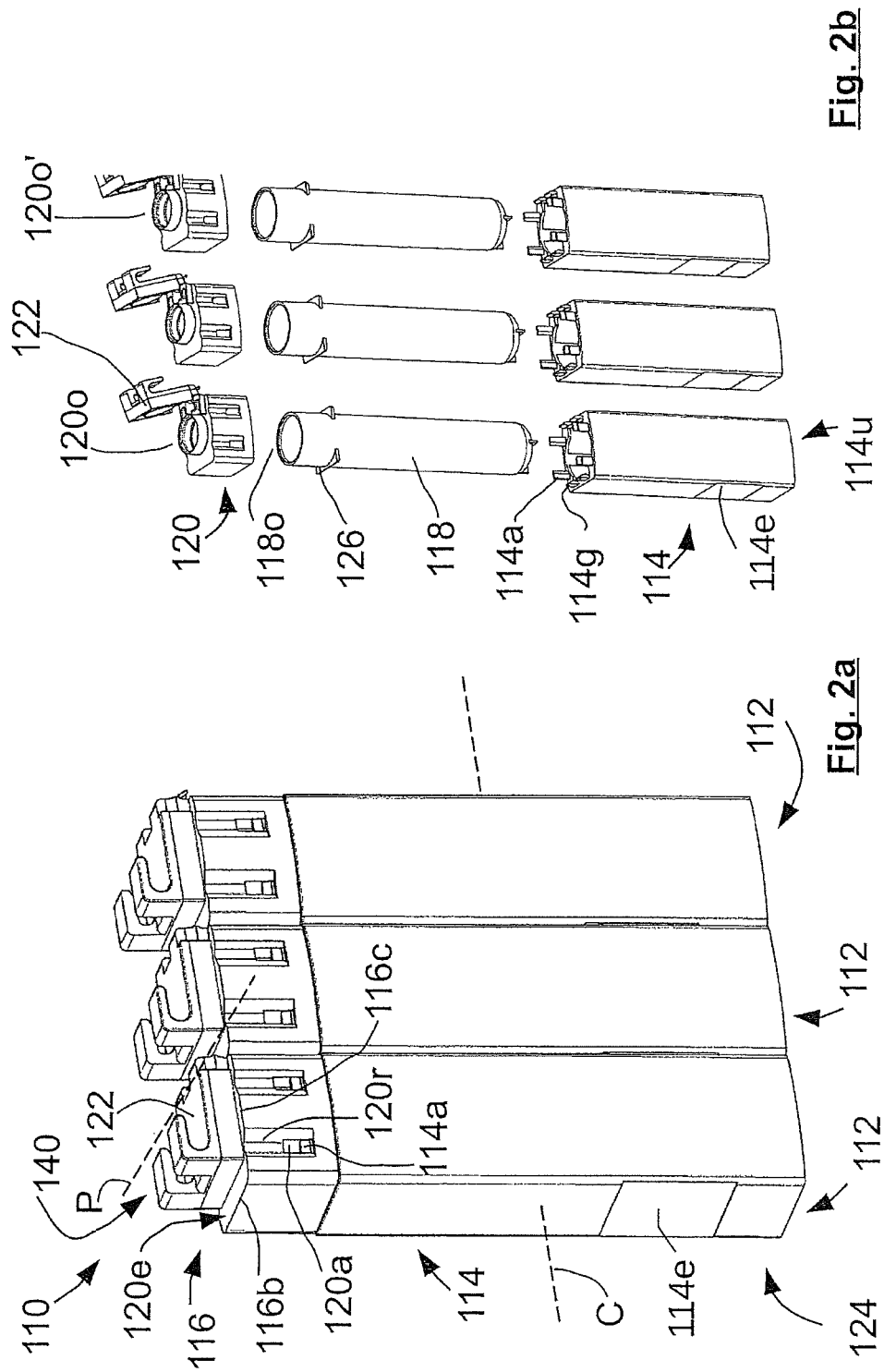

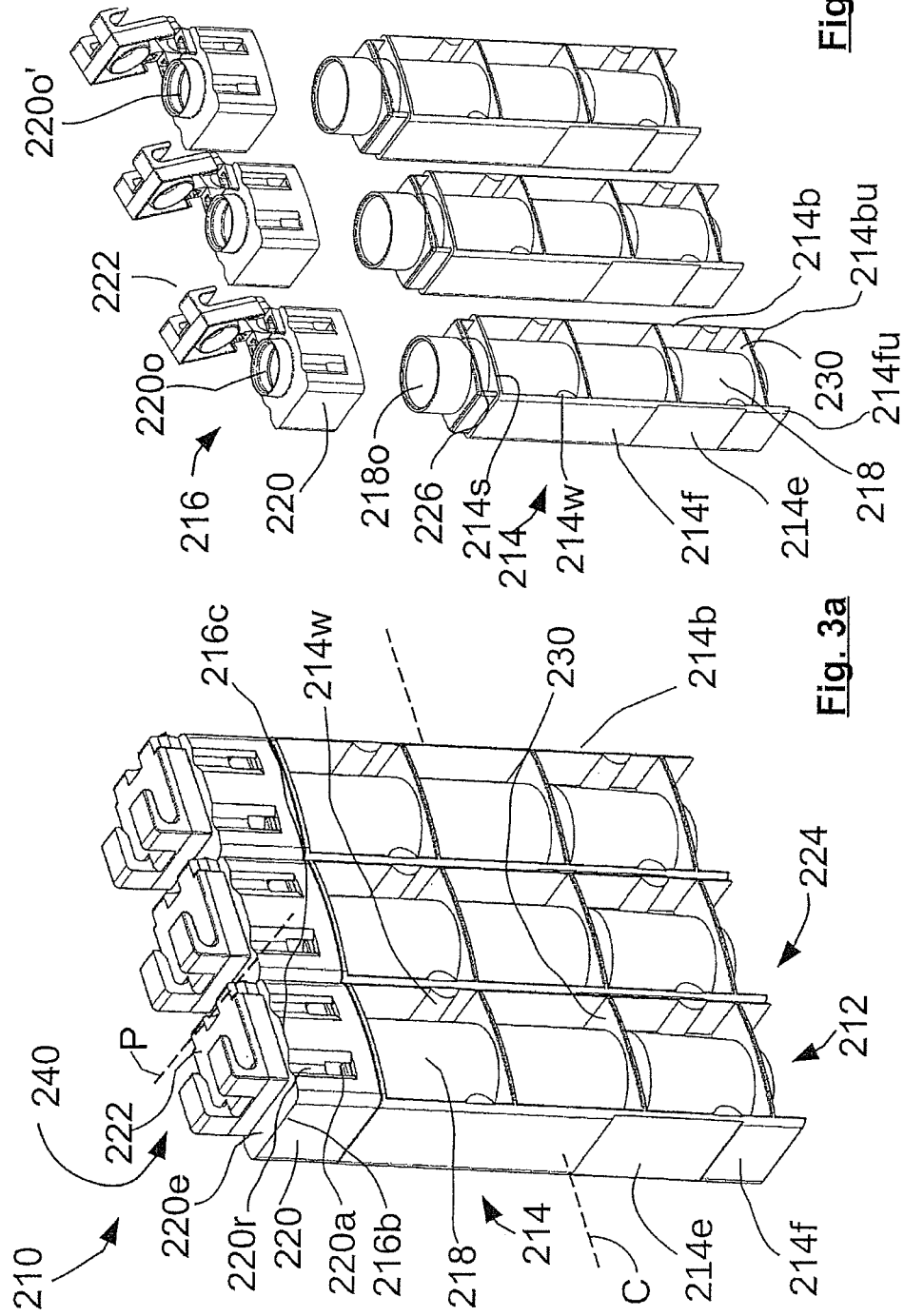

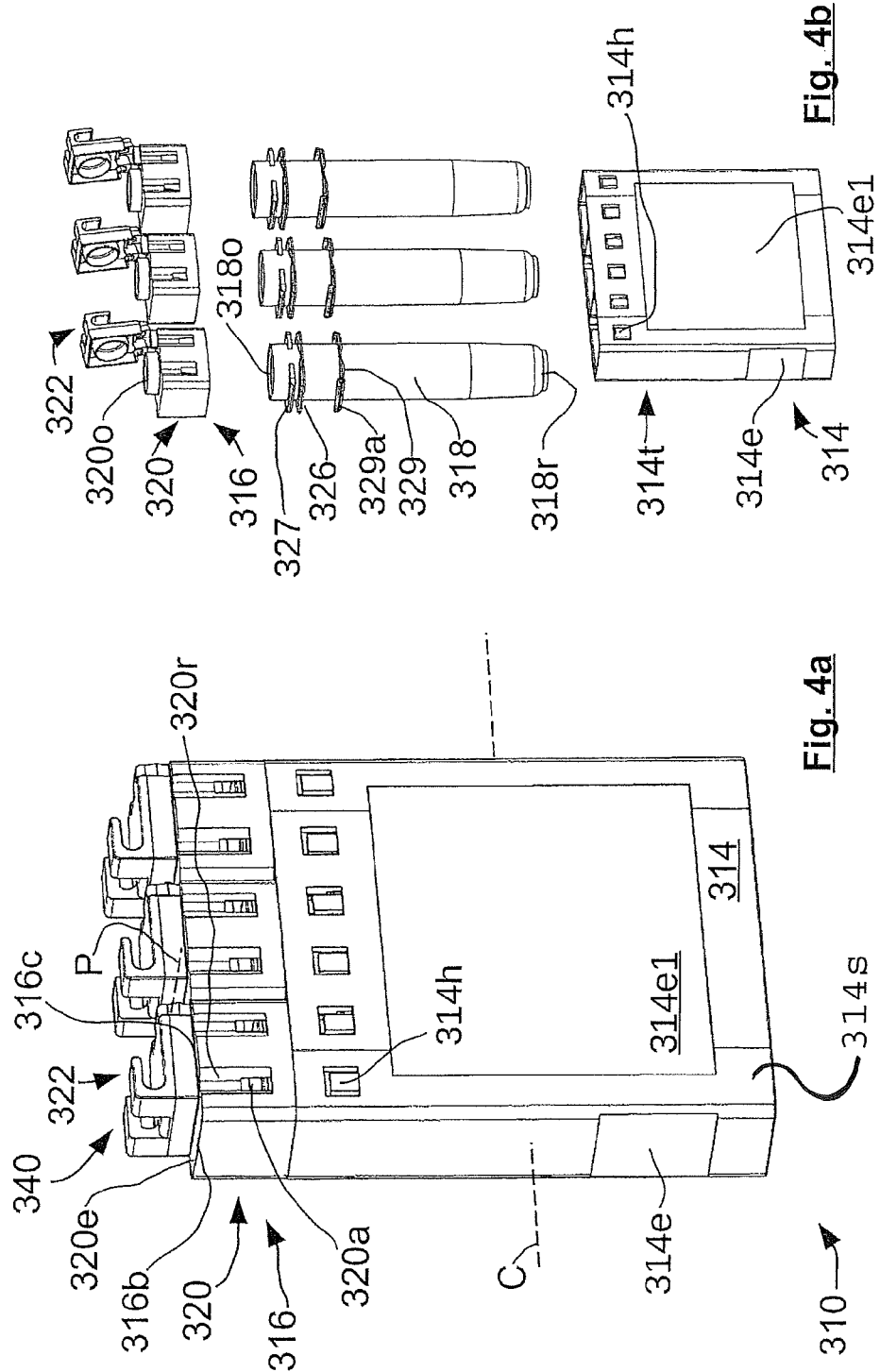

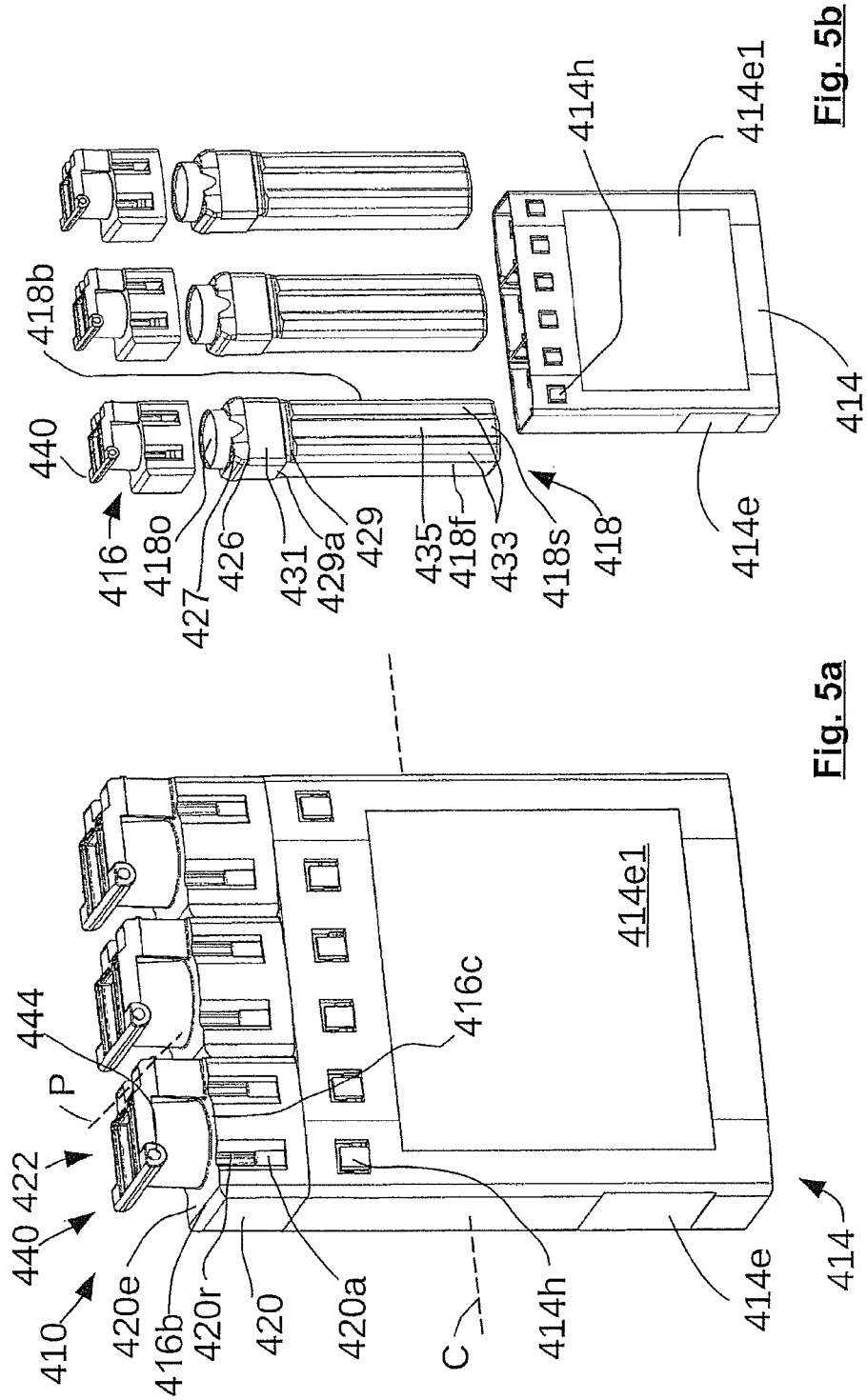

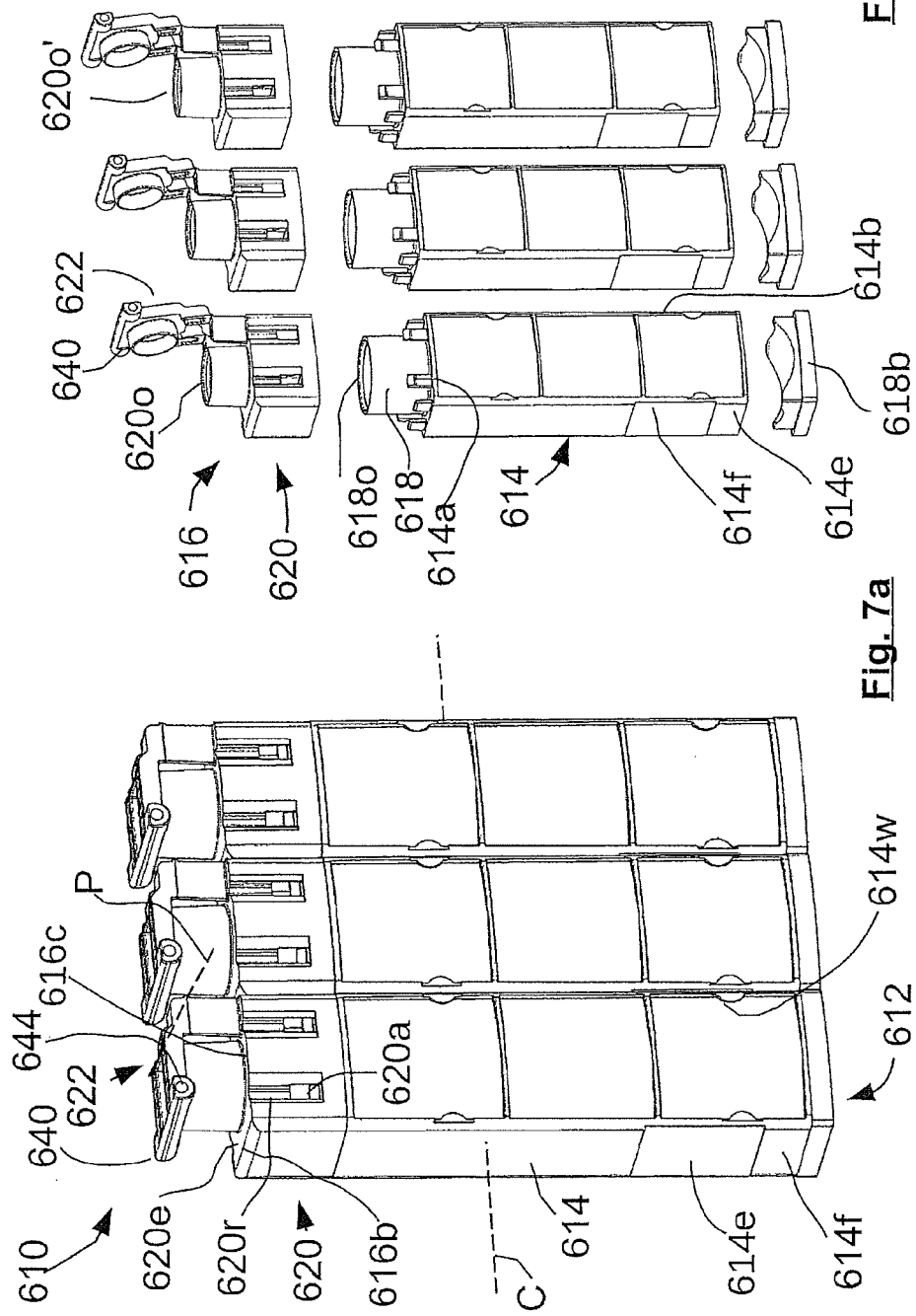

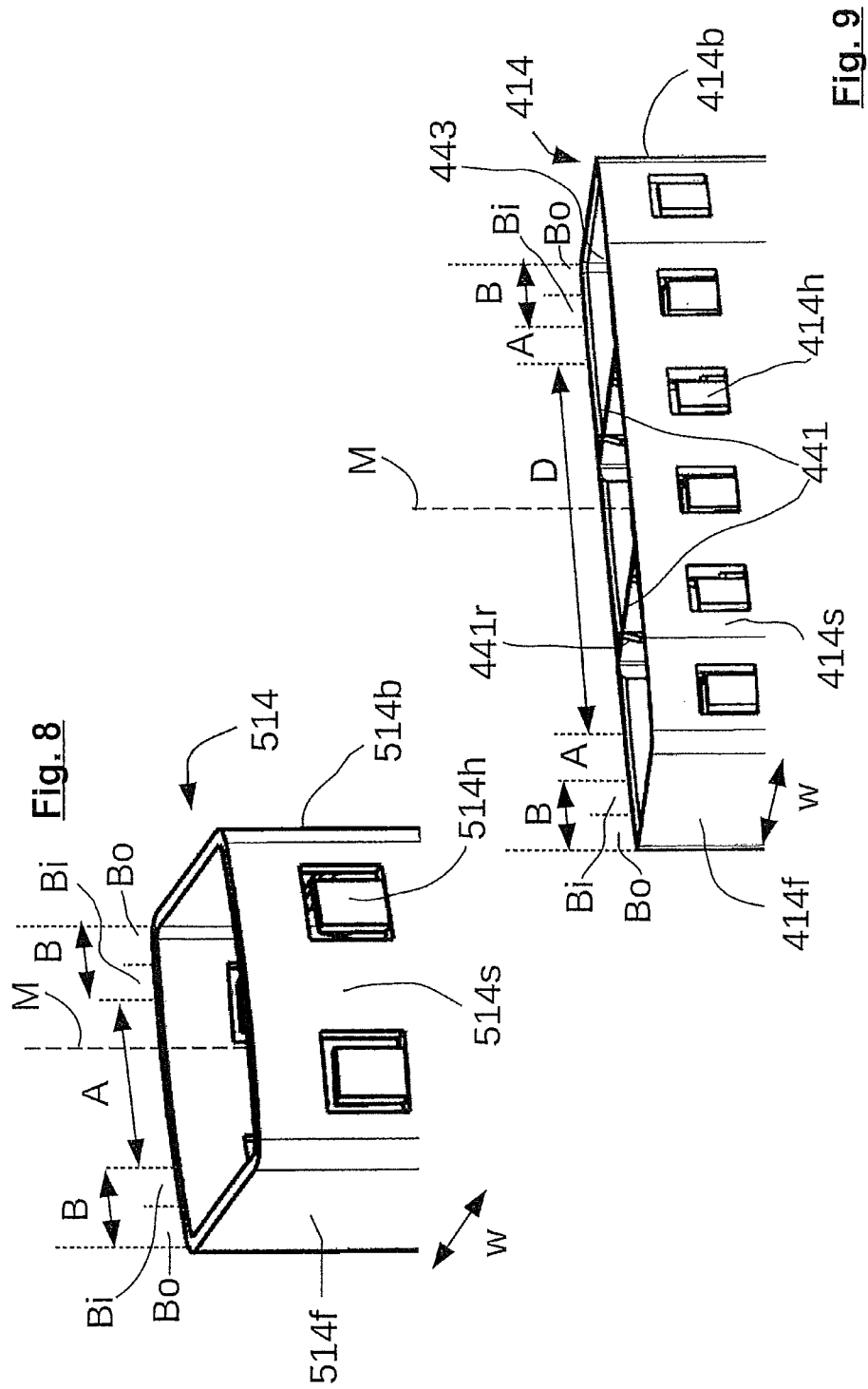

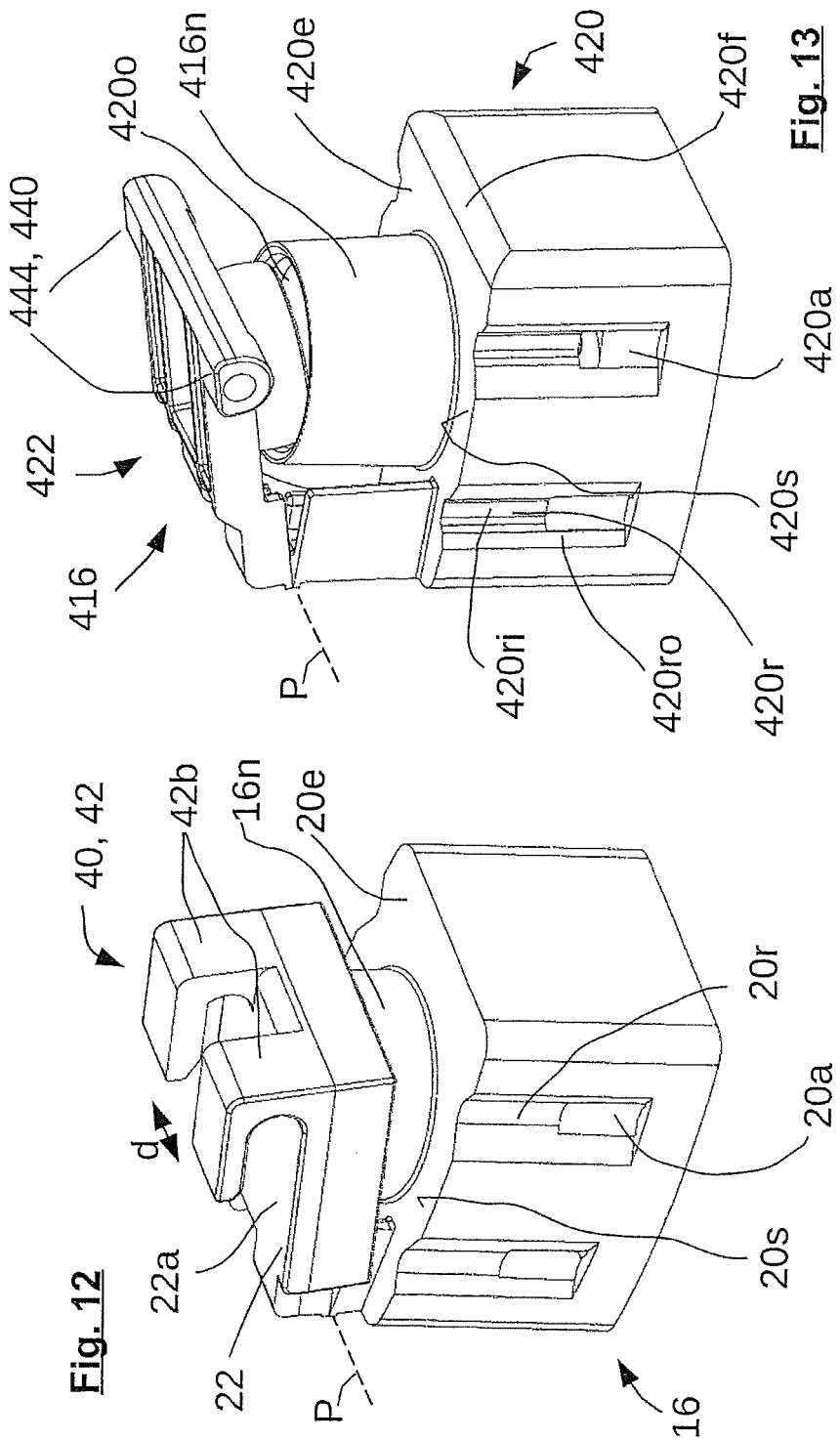

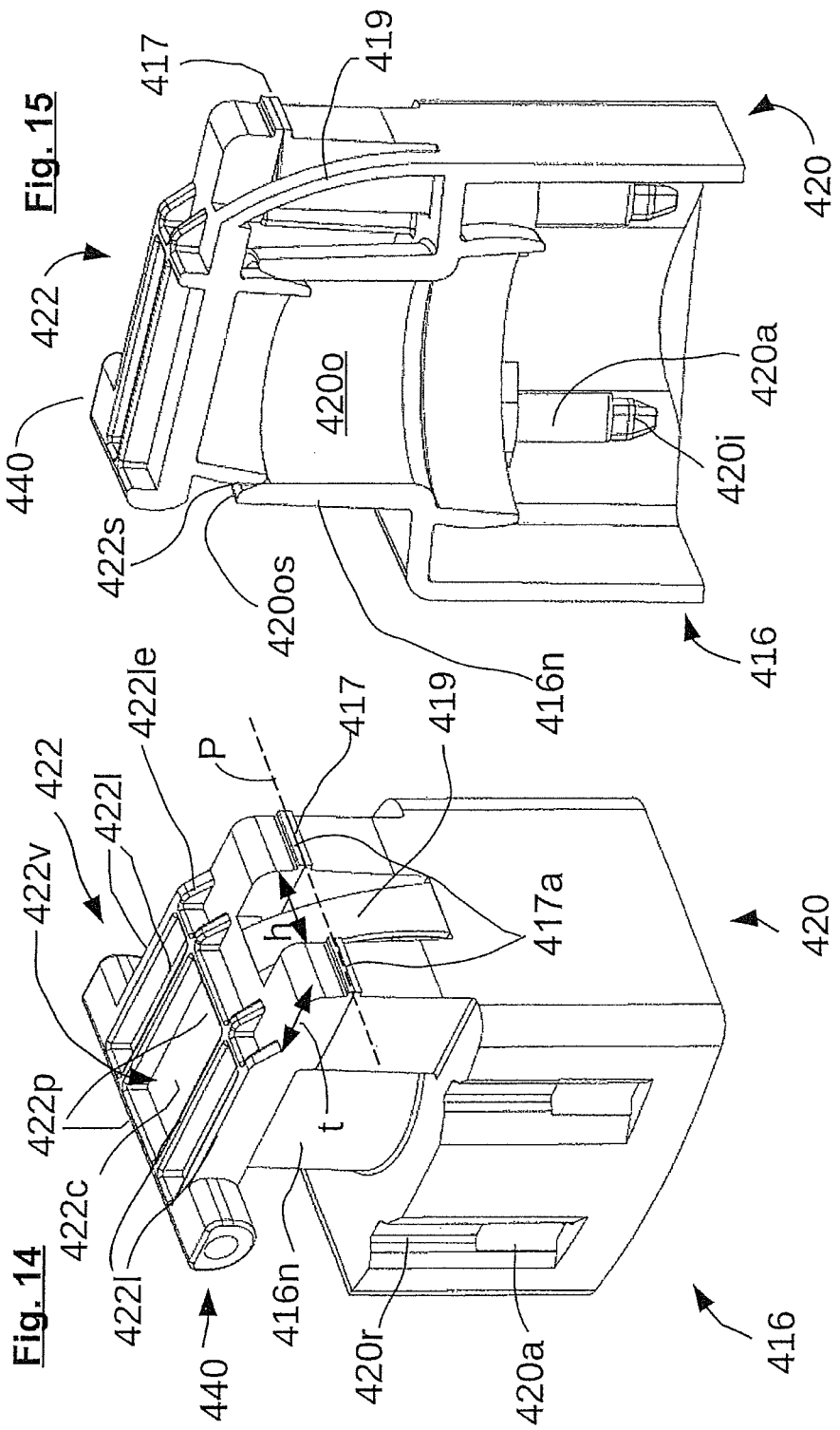

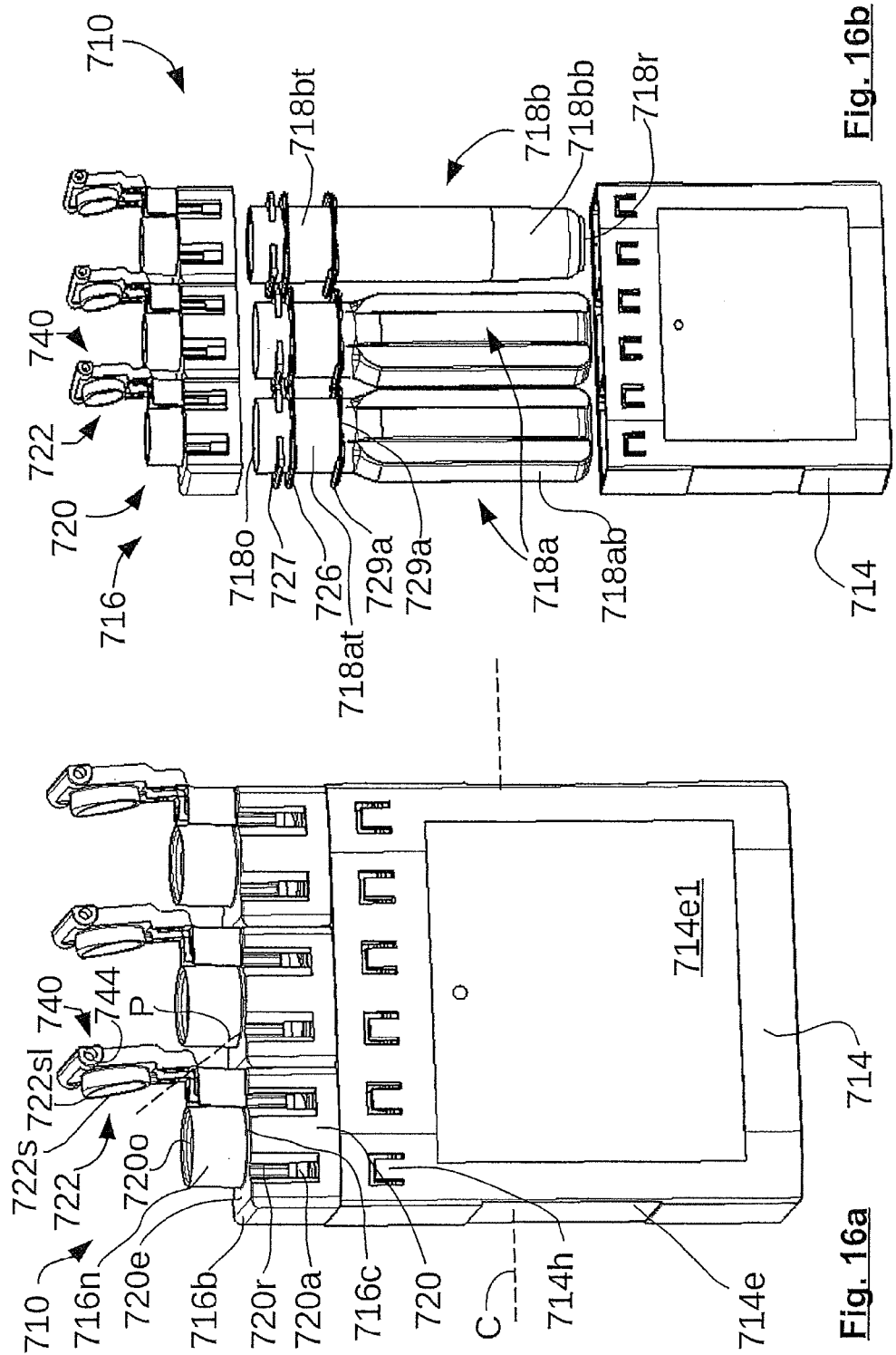

REAGENT KIT FOR ANALYZING APPARATUS

CROSS-REFERENCE TO RELATED APPLICATIONS

This application is a continuation of International Application No. PCT/EP2010/062116, filed 19 Aug. 2010, which claims the benefit of European Patent Application No. 09168175.9, filed 19 Aug. 2009, the disclosure of which is hereby incorporated by reference in its entirety.

BACKGROUND

The instant disclosure is directed to reagent kits and, in particular, reagent kits for analyzing apparatus.

Reagent kits are used in analyzing apparatuses performing a multitude of, e.g., biochemical tests, on a multitude of mostly fluid samples. Therein, the different reagent containers of a reagent kit can, e.g., contain reagents that are needed for one and the same test to be carried out by the analyzing apparatus.

The number of different tests that can be performed by one and the same analyzing apparatus as well as the number of samples that can be tested per hour are key figures defining the performance of the analyzing apparatus. Such figures depend on the number of different reagents and thus different reagent containers that can be provided on the analyzing apparatus.

SUMMARY

It is against the above background that the embodiments of the present invention provide certain unobvious advantages and advancements over the prior art. In particular, the inventor have recognized a need for improvements in reagent kits for analyzing apparatus.

Although the embodiments of the present invention are not limited to specific advantages or functionality, it is noted that the present disclosure provides a reagent kit that makes available more reagent containers on an analyzing apparatus of given size than is possible with current reagent kits.

In accordance with one embodiment, a reagent kit, adapted for use in an analyzing apparatus is provided having a pipetting device and a reagent container opening/closing device. The reagent kit comprises a plurality of reagent containers, each with a top-side opening, and a common reagent container support structure, or a plurality of reagent container support structures, in the latter case each of the reagent container support structures being associated to one of the reagent containers, and wherein each reagent container is mountable or provided on the common or the associated reagent container support structure. The reagent container furthermore comprises a plurality of reagent container caps, each of which is associated to one of the reagent containers and is mountable or provided on the associated reagent container support structure. In a plan view on the top side of the reagent kit, each reagent container cap is formed essentially rectangular, with two shorter edges and two longer edges, and wherein each reagent container cap comprises a cap body and a lid hinged to the cap body so as to be pivotable around a pivot axis at least between a closed position and an opened position, wherein the pivot axis is essentially parallel to the shorter edges of the reagent container cap. Furthermore, each reagent container cap comprises engagement means which are adapted to cooperate with the reagent container opening/closing device in order to pivot the lid between the closed position and the opened position. The reagent containers and the associated reagent container caps are arranged in a row along a connecting line in such a manner that the pivot axes of the reagent container caps are orthogonal to the connecting line, and that, for at least one of the reagent containers, when the at least one reagent container and the associated reagent container cap are provided on the common or the associated reagent container support structure, and when the lid of the associated reagent container cap is in the closed position, in a plan view on the top side of the reagent kit, an end portion of the cap body opposite to the pivot axis is not covered by the lid.

In accordance with another embodiment, an analyzing apparatus is provided comprising a pipetting device, a reagent container opening/closing device and a turntable adapted to receive a plurality of reagent kits configured in accordance with the present disclosure, wherein the reagent kits are arranged on the turntable so that the pivot axes of the reagent container caps are tangential to a circumferential direction of the turntable.

These and other features and advantages of the embodiments of the present disclosure will be more fully understood from the following detailed description taken together with the accompanying claims. It is noted that the scope of the claims is defined by the recitations therein and not by the specific discussions of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which:

FIGS. 1a-b show a first embodiment of a reagent kit according to the present disclosure, FIG. 1a showing a perspective view of the reagent kit in its assembled state, and FIG. 1b showing an exploded perspective view thereof;

FIGS. 2a-b show another typical embodiment of a reagent kit according to the present disclosure, wherein FIG. 2a shows a perspective view of the reagent kit in its assembled state, and FIG. 2b shows an exploded perspective view thereof;

FIGS. 3a-b show yet another typical embodiment of a reagent kit according to the present disclosure, wherein FIG. 3a shows a perspective view of the reagent kit in its assembled state, and FIG. 3b shows an exploded perspective view thereof;

FIGS. 4a-b show still another typical embodiment of a reagent kit according to the present disclosure, FIG. 4a showing a perspective view of the reagent kit in its assembled state, and FIG. 4b showing an exploded perspective view thereof;

FIGS. 5a-b show yet still another typical embodiment of a reagent kit according to the present disclosure, FIG. 5a showing a perspective view of the reagent kit in its assembled state, and FIG. 5b showing an exploded perspective view thereof;

FIGS. 7a-b show even another typical embodiment of a reagent kit according to the present disclosure, FIG. 7a showing a perspective view of the reagent kit in its assembled state, and FIG. 7b showing an exploded perspective view thereof;

FIG. 8 shows a detail of FIG. 6b;

FIG. 9 shows a detail of FIG. 5b;

FIG. 10 shows a perspective sectional view of a part of FIG. 4a;

FIG. 11 shows a perspective sectional view of a part of FIG. 5a

FIG. 12 shows a perspective view of the reagent container cap of the reagent container kit according to some of the embodiments of the present disclosure;

FIG. 13 shows a perspective view of a modified reagent container cap according to an embodiment of the present disclosure;

FIG. 14 shows another perspective view of the subject of FIG. 13;

FIG. 15 shows a perspective sectional view of the subject of FIG. 13;

FIGS. 16a-b show yet even another typical embodiment of a reagent kit according to the present disclosure, FIG. 16a showing a perspective view of the reagent kit in its assembled state, and FIG. 16b showing an exploded perspective view thereof;

Figure 6B:
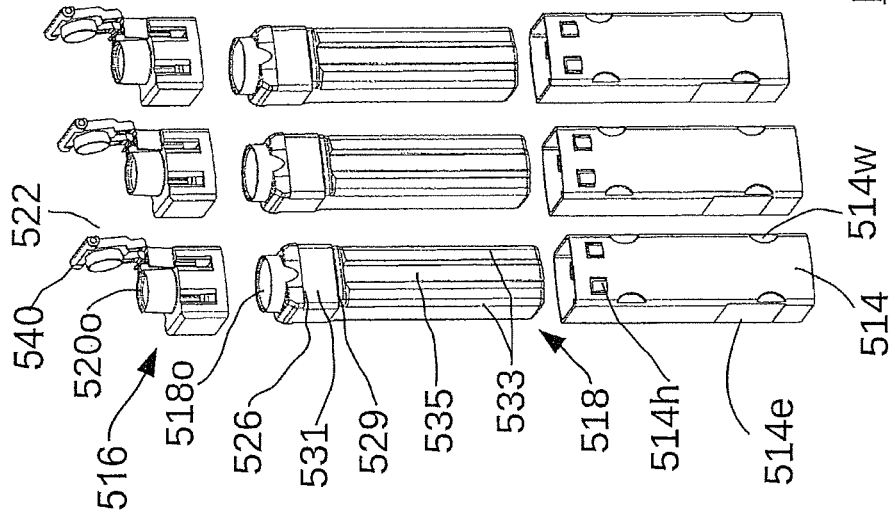
FIGS. 6a-b show still yet another typical embodiment of a reagent kit according to the present disclosure, FIG. 6a showing a perspective view of the reagent kit in its assembled state, and FIG. 6b showing an exploded perspective view thereof.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present disclosure.

DETAILED DESCRIPTION

The reagent containers are adapted to contain a typically fluid reagent. However, the present disclosure relates to reagent kits with reagent containers regardless of the question whether the reagent containers are filled with a reagent or whether they are empty.

A generic reagent kit is provided, wherein the reagent containers and associated reagent container caps are arranged in a row along a connecting line in such a manner, that the pivot axes of the reagent container caps are orthogonal to the connecting line, and wherein, for at least one of the reagent container caps, when the at least one reagent container and the associated reagent container cap are provided on the common or the associated reagent container support structure, and when the lid is in the closed position, in a plan view on the top side of the reagent kit, an end portion of the cap body opposite to the pivot axis is not covered by the lid.

Throughout the present disclosure, whenever directions are mentioned, those directions relate to a reagent container or reagent container kit under normal operating conditions, i.e., the reagent container standing upright, its opening provided on the top side.

Furthermore, if a feature is described throughout the present disclosure "for at least one of the reagent containers", this feature can also apply to more than one, typically to all reagent containers (or to the reagent container caps associated thereto, etc.) of a reagent kit according to the present disclosure.

Since, according to the present disclosure, the reagent containers and the reagent container caps are arranged in a row along a connecting line in such a manner that the pivot axes of the reagent container caps are orthogonal to the connecting line and since, for at least one of the reagent containers, in a plan view on the top side of the reagent kit, an end portion of the cap body of the associated reagent container cap opposite to the hinge is not covered by the lid in its closed position, this end portion of the cap body can be used to receive the opened lid of a reagent container immediately adjacent to the at least one reagent container described before.

Thus, the length of the reagent kit along the connecting line can be minimized, allowing to place more different reagent containers on an analyzing apparatus of given size than it was possible previously.

The embodiments of the present disclosure can be employed with analyzing apparatuses having a turntable for receiving the reagent kits. Therein, different reagent kits according to the disclosure can be arranged radially on the turntable and since the pivot axes are orthogonal to the radially extending connecting line, and since the width of the reagent kits orthogonal to the connecting line of the reagent containers is defined mainly by the width or diameter of the reagent containers, the number of reagent containers and/or reagent container kits that can be provided on such a turntable is considerably increased.

In order to facilitate fabrication and assembly, for at least one of the reagent containers, the cap lid of the associated reagent container cap can be integrally formed with the cap body and linked to the cap body by a film hinge or integral hinge, in particular if the cap is formed by injection molding.

For at least one of the reagent containers, typically for several or for all reagent containers, the common or associated reagent container support structure and the at least one reagent container can be separately formed and the at least one reagent container can be adapted to be snapped or welded to the common or associated reagent container support structure, which makes the manufacture and the assembly of the reagent kit easy.

The common or associated reagent container support structure, formed separately from the at least one reagent container, can enclose the reagent container on all sides with exception of the upper side having the opening. However, it can be typical that the reagent container support structure does not cover the underside of the reagent container in order to ensure a minimum of air circulation when the reagent kit is mounted in the analyzing apparatus so that a suitable thermal contact between the content of the reagent container and the environment of the analyzing apparatus can be achieved.

Alternatively, for at least one of the reagent containers, the common or associated reagent container support structure and the at least one reagent container can be integrally formed. In this case, the reagent container/reagent container support structure can for example include a front wall and a back wall and lateral rib-like or ring-like structures connecting the front wall and the back wall. In this way, the number of required parts as well as the amount of material needed is considerably reduced. Furthermore, this open structure ensures a good thermal contact to the environment. The front wall and the back wall provide stability and can be used to fix neighboring reagent containers to each other.

When the common or the associated reagent container support structure and the at least one of the reagent containers are separately formed, the reagent container support structure and the reagent container cap associated to the at least one reagent container can be integrally formed, again reducing the number of required parts and facilitating the assembly of the reagent kit.

Alternatively, for at least one of the reagent containers, the common or associated reagent container support structure and the associated reagent container cap can be separately formed and the associated reagent container cap can be adapted to be snapped on the common or the associated reagent container support structure or on the at least one reagent container.

In this case, the different parts constituting the reagent container kit can be smaller and geometrically less complex than in the case when the reagent container support structure and cap are integrally formed and thus, those parts can be more easily manufactured, e.g., by injection molding.

In many cases, a plurality of different reagent containers, often, e.g., three reagent containers, are necessary for one and the same test. The reagent kit can comprise two to six, typically three to five, most typically three reagent containers.

In order to reduce the number of required parts and to facilitate assembly, the reagent containers and reagent container caps can be mounted or are mountable to one and the same common reagent container support structure, the reagent kit thus containing all reagents needed for one test when the reagent containers are filled.

Alternatively, the reagent kit can comprise a plurality of reagent container support structures, each reagent container support structure associated to one of the reagent containers, wherein the reagent container support structures are arranged in a row along the connecting line and adjacent reagent container support structures can be fixed to each other, forming a reagent container support structure unit.

Particularly stable support structure units can be obtained by fixing adjacent reagent container support structures to each other, e.g., by ultrasonic welding.

Concerning the mounting of a separately formed cap body to a reagent container support structure, for at least one of the reagent containers, the cap body of the associated reagent container cap can typically comprise a snap opening and the common or the associated reagent container support structure can comprise a snap hook adapted to snap into the snap opening when the associated reagent container cap is mounted to the reagent container support structure. Of course, also other types of snap-fit structures are possible. Alternatively or additionally, the cap can also be mounted to the reagent container via a similar snap closure. Such mounting structures are easy to manufacture and to assemble.

Furthermore, in this case, the surface of the cap body of the reagent container cap associated to the at least one reagent container can have a recessed portion immediately above the snap opening. By providing such a recessed portion immediately above the snap opening, no sliding parts are needed in the injection mold in order to form the cap body, thus simplifying the fabrication process and lowering the fabrication cost.

Furthermore, this recessed portion of the surface of the cap body can be used in order to cooperate with a suitable positioning device of the analyzing apparatus which ensures that the reagent kit is in the desired position within the apparatus. The positioning device can, e.g., comprise a leaf spring or a spring-biased roller which engages the recessed portion when the reagent kit is in its desired position. The recessed portion or an outer portion thereof can be essentially V-shaped, e.g., with an included angle of about 120°.

Structures formed on the reagent container, the reagent container support structure and the cap for mounting the different parts to each other, such as the snap openings and snap hooks addressed above, are typically formed so that different types of containers, caps and support structures can be mounted to each other. In this case, e.g., the same type of cap or the same type of reagent container support structure can be used for different types of reagent containers, enhancing the flexibility of the system and lowering the production costs as less different molding devices are needed.

The reagent kit is configured such that it can be inserted into the analyzing apparatus and removed from it after the reagents in the reagent containers have been used or are past their expiration date. In those analyzing apparatuses, the different kits are usually arranged linearly or radially so that a reagent kit to be inserted has to be inserted between two neighboring reagent kits. In order to facilitate this insertion, the common reagent container support structure or the reagent container support structure unit can have at least one tapered end portion along the connecting line.

When used in the analyzing apparatus, the reagent containers will be frequently opened and closed. The force thereby acting on the cap lids will also at least partially act on the reagent container and reagent container kit as a whole. In order to prevent that the reagent kit is thereby displaced from its desired position, for at least one of the reagent containers, an upper surface of the cap body of the associated reagent container cap can comprise two shoulder portions formed adjacent to the edges orthogonal to the pivot axis which, in a plan view on the top side of the reagent kit, are not covered by a lid in its closed position. Those portions which are not covered by the lid in its closed position can be used by a suitable stopping device provided on the analyzing apparatus above those shoulder portions of the cap body when the reagent kit is mounted in the analyzing apparatus, wherein those stopping devices prevent a reagent kit from being displaced upwards when the lid of a cap provided on the reagent kit is opened.

In order to cooperate with the reagent container opening/closing device provided on the analyzing apparatus, for at least one of the reagent containers, the engagement means of the associated reagent container cap can comprise a hook formed on the upper side of the lid adjacent to the edge of the lid opposite to the pivot axis, wherein the hook is bent towards the pivot axis. In this way, the engagement means, i.e., the hook, can be engaged by a stirrup-shaped engaging means provided on the opening/closing device. The engagement time of such a stirrup-shaped engaging means is very short as it is only necessary to move it along a very short way in order to engage it with or disengage it from the hook.

Furthermore, if the hook and the corresponding stirrup-shaped engaging means are suitably constructed, relatively high tolerances between immobile and rotating parts of the analyzing apparatus can be compensated.

Alternatively, the engagement means can comprise two essentially bar-shaped protrusions, protruding from the lid essentially parallel to the pivot axis and being formed on the lid adjacent to the edge of the lid opposite to the pivot axis.

This form of the engagement means, in contrast to the hook-shaped form described above, is less prone to unintentionally get caught with other objects during assembly, handling, etc. In combination with a correspondingly formed engaging means provided on the analyzing apparatus, similar effects can be obtained as with a hook-shaped engagement means.

The reagent kits according to the embodiments of the present disclosure comprise different parts (e.g., containers, caps and support structures) that are usually prefabricated in large numbers and automatically assembled.

In order to facilitate this assembly, it is typical that the parts are as symmetrical as possible. In particular, at least one of the reagent containers and/or the common or associated reagent container support structure can have a twofold rotational symmetry with respect to their respective vertical middle axis, i.e., look the same when rotated about this axis by 180°.

This symmetry is only broken when the cap is mounted to the reagent container, the position of the pivot axis determining front side and back side.

Once the reagent containers are filled with a reagent, it is typical to label the containers according to their content and if necessary, e.g., according to their batch number. It is also contemplated that reagent containers could be labeled and afterwards filled with a reagent. The same applies to a test assembled in a reagent kit. The labels should typically be easily accessible and machine-readable as well as readable by a user. Therefore, for at least one of the reagent containers, the common or associated reagent container support structure and/or the associated reagent container cap can comprise one or several regions adapted to be marked, e.g., by a stick-on label or to be printed on. If the container support structure or cap is to be marked by a stick-on label, it can be configured such that this region is recessed. If desired, a further label, e.g., a RFID-tag, can disposed in a protected position in the recessed region, sandwiched between the recessed region and the stick-on label, for instance.

Typically, a plurality of reagent kits as described above are integrated into an analyzing apparatus, the apparatus comprising a pipetting device, a reagent container opening/closing device and a turntable adapted to receive a plurality of reagent kits, wherein the reagent kits are arranged on the turntable, so that the pivot axes of the reagent container caps are tangential to a circumferential direction of the turntable.

As explained above, in this way, the number of reagent containers that can be provided on an analyzing apparatus of given size can be considerably increased.

FIG. 1a shows a reagent kit 10 according to a first embodiment of the present disclosure.

The reagent kit 10 comprises three reagent kit units 12 which can be essentially identical but can also differ from each other. As in the present case, all three reagent kit units 12 are very similar, in the following only one reagent kit unit 12 is provided with reference signs for reasons of clarity.

Each reagent kit unit 12 comprises a reagent container support structure 14 integrally formed with a reagent container cap 16 on which a reagent container 18 is mounted.

Each reagent container support structure 14 comprises a front wall 14f and a back wall 14b which are planar and parallel to each other, and two side walls 14s which may be slightly curved. However, the reagent container support structure 14 has no mold releasing slopes on its outer structure which can be advantageous during transport and handling. The front wall 14f can comprise a recessed portion 14e on which a label for marking the content of the reagent kit unit 12 can be disposed.

The reagent container 18 is more clearly shown in the exploded view of FIG. 1b, whereas in FIG. 1a only the snap hooks 18a of the reagent container 18 are visible. In the assembled state shown in FIG. 1a those snap hooks are snapped into snap openings 20a provided on cap bodies 20 of the reagent container caps 16.

The reagent container caps 16 each comprise a cap body 20 and a cap lid 22 hinged to the top side of the cap body 20 so as to be pivotable around a pivot axis P. Cap body 20 and cap lid 22 can be integrally formed and connected by a film hinge not visible in the figures.

In a plan view on the top side the caps 16 are formed essentially rectangular having two shorter edges 16b and two longer edges 16c each. The cap lids 22 are provided on the cap body 20 so that the pivot axes P are parallel to the shorter edges 16b of the cap 16 and the three reagent kit units 12 are arranged in a row along a connecting line C that is orthogonal to the pivot axis P.

FIG. 1a shows all cap lids 22 in their closed position. In this position, in a plan view on the top side of the reagent kit 10, an end portion 20e of each cap body 20 is not covered by the lid 22. This end portion 20e serves to receive the cap lid 22 of the adjacent cap 16 when it is in its opened position. This allows to arrange the reagent kit units 12 in a very space-saving manner.

The snap opening 20a of each cap body 20 is positioned directly under a recessed portion 20r of the cap body 20 which can be used to cooperate with a suitable positioning device provided on the analyzing apparatus.

In this way, the positioning device as well as the reagent kits can be arranged in a very space saving manner on a turntable of a given analyzing apparatus.

The snap opening 20a in combination with the recessed portion 20r can furthermore be used to receive snap hooks provided on a reagent kit cover (not shown) that can typically be used during transport of the reagent kit in order to prevent the cap lids from getting caught with other objects and in order to ensure that the reagent containers 18 remain closed.

The structure of the cap lids 22 will be explained in detail with respect to FIGS. 12 to 15.

The three reagent container support structures 14 shown in FIG. 1a can be fixed to each other for example by ultrasonic welding, thus forming a reagent container support structure unit 24.

FIG. 1b shows the subject of FIG. 1a in an exploded perspective view wherein furthermore the cap lids 22 are opened. In this exploded view, the reagent containers 18 are fully visible. The reagent containers 18 include a mounting plate 26 which is provided with the snap hooks 18a mentioned above for fixing the reagent containers 18 to the reagent container support structures 14.

Furthermore, FIG. 1b shows that the cap bodies 20 are provided with cap body openings 20o placed over the openings 18o of the reagent containers 18. One of these cap body openings 20o' has a larger diameter than the others. The diameter of the cap body openings 20o can depend on the (future) content of the reagent containers. Some containers may be filled with substances comprising, e.g., beads or other sediments which have to be regularly mixed in the reagent container 18 by a suitable mixing device. As the diameter of the mixing device is usually larger than the diameter of the pipetting device, the cap body opening 20o' of a reagent container which contains a substance that has to be mixed can be larger than the diameter of the cap body opening 20o of the other reagent containers 18.

FIGS. 2a-b show a reagent container kit 110 according to a second embodiment of the present disclosure. FIG. 2a shows the reagent container kit 110 in a perspective view, and FIG. 2b shows it in an exploded perspective view, corresponding to the views of FIGS. 1a and 1b.

In the following, features of several further embodiments of the disclosure, which correspond to features of the first embodiment shown in FIGS. 1a-b are provided, with reference signs that result from the corresponding reference signs of FIGS. 1a-b, by adding the number 100, 200, 300, 400, 500, 600 and 700 for the second, third, fourth, fifth, sixth, seventh and eighth embodiment, respectively.

The following embodiments are only described in detail insofar as they differ from the first embodiment shown in FIGS. 1a-b, or from each other. With respect to the corresponding features, reference is made to the description of the first embodiment above or to the description of the first embodiment that shows a specific feature.

The reagent kit 110 according to the second embodiment differs from that of the first embodiment mainly in that the reagent container support structure 114 and the reagent container cap 116 are separately formed. The reagent container support structure 114 comprises four snap hooks 114a that engage with snap openings 120a formed in the cap body 120 of the reagent container cap 116. Furthermore, each reagent container support structure 114 comprises four snap hooks 114g that are adapted to engage the mounting plates 126 formed on the reagent containers 118.

As shown in FIG. 2b, the reagent containers 118 can be inserted into the reagent container support structures 114 from above and fixed to them via a snap closure. Afterwards, the reagent container caps 116 can be snapped onto the reagent container support structures 114.

Furthermore, after assembly the reagent container cap 116 secures the snap closure between the hooks 114g and the mounting plate 126, preventing that the reagent container 118 is unintentionally removed from the container support structure 114. Whereas the reagent container support structures 14 of the first embodiment are open on their underside 14u in order to insert the reagent containers 18 from below (cf., FIG. 1b), the reagent container support structures 114 can be closed on their underside 114u as in the reagent kit 110, the reagent containers 118 are inserted from above as shown in FIG. 2b. However, it can be typical that also the reagent container support structures 114 of the reagent kit 110 have open undersides 114u as this facilitates thermal contact with the environment when the reagent kit 110 is placed in an analyzing apparatus.

As shown in FIGS. 3a and 3b, which depict a reagent kit 210 according to a third embodiment of the present disclosure, the reagent container support structure 214 and the reagent container 218 can also be integrally formed. In contrast to the first two embodiments the container support structure 214 does not enclose the reagent container 218 from four sides but comprises only a front wall 214f and a back wall 214b as well as, i.e., three, rib-like or ring-like structures 230 that connect the front wall 214f and the back wall 214b of the reagent container support structure 214 and enclose the, e.g., cylindrical, reagent container 218. The structures 230 can be integrally connected to the reagent container 218 by an inner central vertically extending rib (not shown).

Instead of the snap hooks 114a of FIGS. 2a-b, the reagent container support structure 214 illustrated in FIGS. 3a-b has a snap plate 226 for engaging the snap openings 220a and/or snap structures (not shown) provided below the snap openings 220a on the inner side of the reagent container caps 216. This snap plate 226 is very robust, especially for quick assembly. A stopping plate 214s disposed below the snap plate 226 prevents the cap 216 from being displaced further downwards than shown in FIG. 3a.

The front wall 214f and the back wall 214b are essentially planar (no mold releasing slopes), parallel to each other and the thickness of these walls may be larger in a portion 214fu, 214bu near the bottom of the reagent container support structure 214 in order to enhance its stability. Furthermore, the bottom portion 214fu, 214bu may comprise an L-shaped base part (not shown) improving the stability and rigidity of the reagent container support structure 214.

The reagent container support structures 214 of different reagent containers 218 are welded together on suitable portions 214w on the front and back walls 214f, 214b of the reagent container support structure 214. At the portions 214w of the reagent container support structures 214, an excess of material in form of a horizontal rib is provided to facilitate welding.

This open structure of FIGS. 3a-b is light, easy to fabricate and reduces the amount of material needed for manufacturing the reagent kits.

FIGS. 4a-b show a reagent kit 310 according to a fourth embodiment of the present disclosure. In contrast to the first three embodiments, wherein three reagent container support structures are fixed to each other and form a reagent container support structure unit, in the reagent kit 310 illustrated in FIGS. 4a-b a single common reagent container support structure 314 is employed to receive three reagent containers 318 and their associated reagent container caps 316.

In addition to the recessed portion 314e, the reagent container support structure 314 comprises an additional recessed portion 314e1 disposed on the side wall 314s which is considerably larger than the portion 314e and thus provides more place for information about the content of the reagent kit 310.

As shown in the exploded view of FIG. 4b the reagent containers 318 and the reagent container caps 316 can be preassembled, typically after filling. Afterwards, they can be inserted from above into the reagent container support structure 314.

The reagent container 318 can comprise a ring-like structure 318r at the bottom on which the container 318 can stand on its own, e.g., during weighing after filling, or which can be used by a vacuum gripper of a robotic arm during weighing, transport, assembly, etc.

In contrast to the reagent containers 18 and 118 of the reagent kits 10 and 110, the reagent container 318 comprises a plurality of mounting plates, i.e., a lower mounting plate 329, a middle mounting plate 326 and an upper mounting plate 327.

The part 329a of the lower mounting plate 329 may, in the assembled state, abut from above against a horizontally extending abutment rib (not shown) provided on the inner side of the reagent container support structure 314 in order to position the container 318 in the vertical direction.

Figure 10:
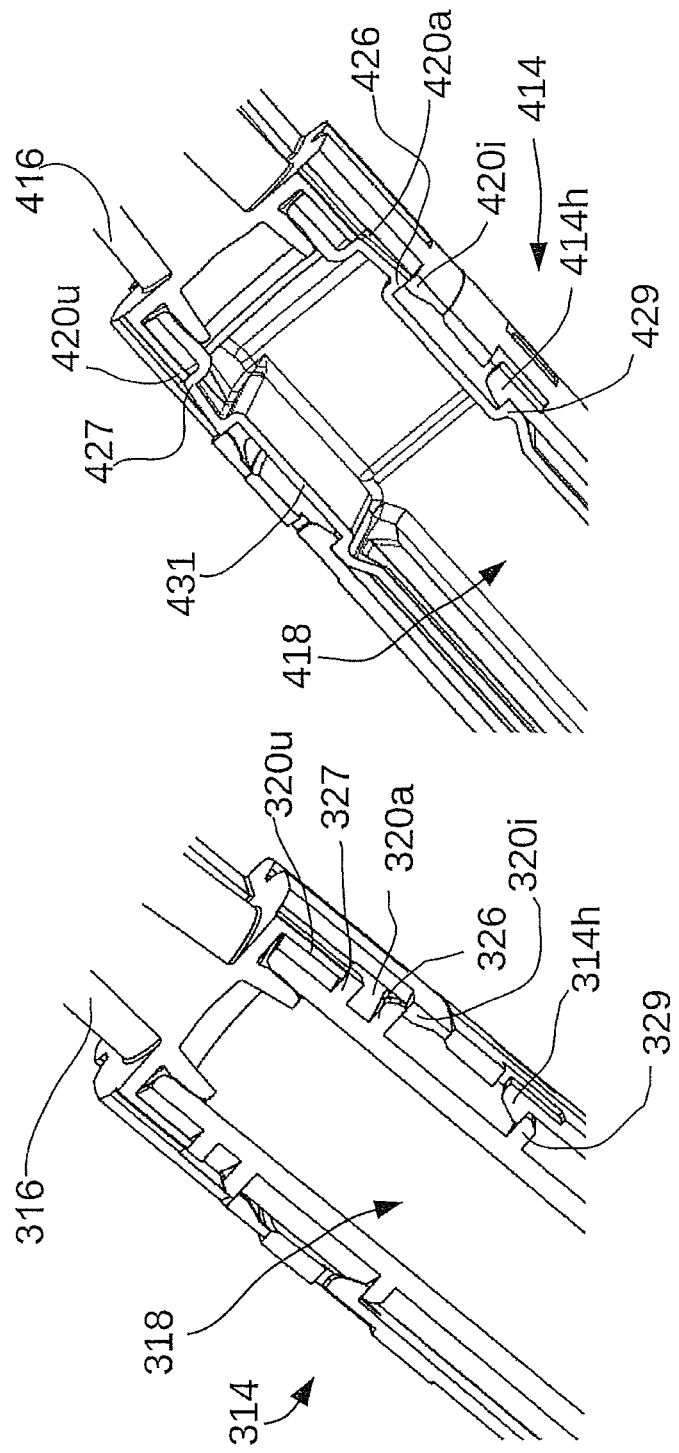

As can be seen more clearly in the sectional view of FIG. 10, the lower mounting plate 329 is adapted to engage with the snap hook 314h provided on the reagent container support structure 314 and the middle mounting plate 326 engages with the snap opening 320a of the cap body 320 and with a snap structure 320i provided on the inner side of the cap body 320.

The upper mounting plate 327 is adapted to abut against a stop element 320u of the cap 316 (cf., FIG. 10), thus ensuring that the cap 316 is not displaced further downward than shown in the figure.

The mounting plates can be slightly chamfered according to the mounting direction in order to facilitate assembly.

If, during handling, two opposite walls of the cap 316 mounted to the reagent container 318 are pressed together (e.g., the front wall and the back wall), the other two walls (e.g., the side walls) could bulge out, resulting in an (involuntary) disengagement between the middle mounting plate 326 and the snap opening 320a/inner snap structure 320i provided on the cap body 320 (cf., FIG. 10). In order to prevent this, the middle mounting plate can abut against all four inner walls of the cap body 320 (cf., FIG. 10), preventing the walls from being pressed together and therefore preventing the other walls from being bulged out.

The bottom of the inner volume of the reagent container 318 may be rounded in order to allow mixing of fluids within the container.

Furthermore, FIG. 4b shows that end portions 314t of the reagent container support structure 314 are slightly tapered in order to facilitate inserting a reagent kit 310 between two other reagent kits in the analyzing apparatus.

The main difference between the reagent kit 310 shown in FIGS. 4a-b and the reagent kit 410 shown in FIGS. 5a-b is that the reagent containers 418 of reagent kit 410 have a considerably larger inner volume than the reagent containers 318 of reagent kit 310.

Those reagent containers 418 are often used for diluents or other substances which are frequently needed in the tests performed on an analyzing apparatus. They can be produced, e.g., by extrusion blow molding.

Each reagent container 418 has a front wall 418f, a back wall 418b and two side walls 418s, the width of the side walls 418s being larger than that of the front and back walls 418f, 418b. The inner section of such a reagent container 418 can also be essentially rectangular in order to use the available space efficiently.

The side walls 418s can comprise a protruding central and vertically extending part 435 for positioning and guiding the reagent container 418 with respect to the reagent container support structure 414.

Near the top opening 418o of the reagent container 418, the side walls 418s can comprise a recessed neck portion 431 with an upper snap edge 426 and a lower snap edge 429 provided at the upper or lower end of the neck portion 431.

As it is more clearly shown in the sectional view of FIG. 11, the lower snap edge 429 is adapted to engage the snap hooks 414h provided on the reagent container support structure 414 and the upper snap edge 426 is adapted to engage in the snap opening 420a provided in the cap body 420 and with the inner snap structure 420i provided on the inner side of the cap body 420 below the snap opening 420a. Finally, a further edge 427 has the same function as the upper mounting plate 327 of reagent container 310 shown in FIG. 10.

In order not to interfere with the snap hooks 414h when the reagent container 418 is inserted into the reagent container support structure 414 from above, a vertically extending recessed portion 433 is provided on both sides of the central part 435 (cf., FIG. 5b).

Figure 11:
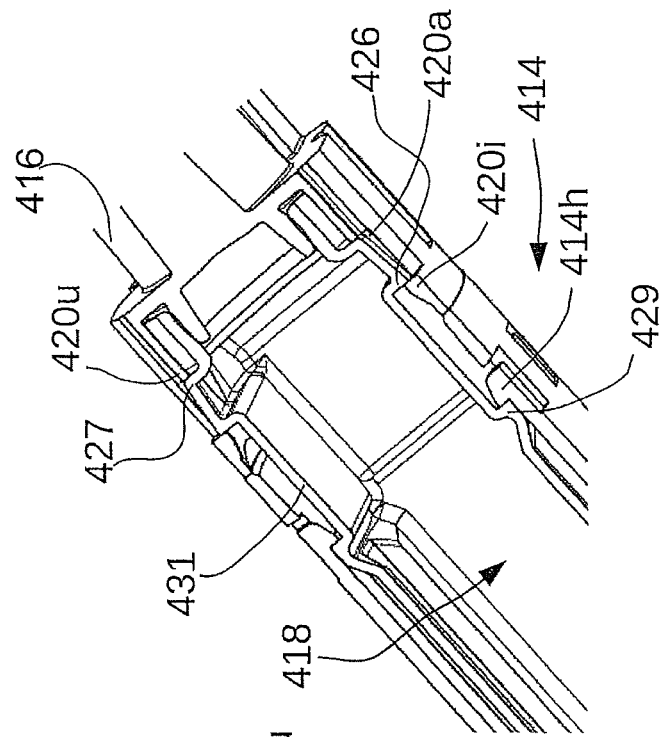
Figure 17:
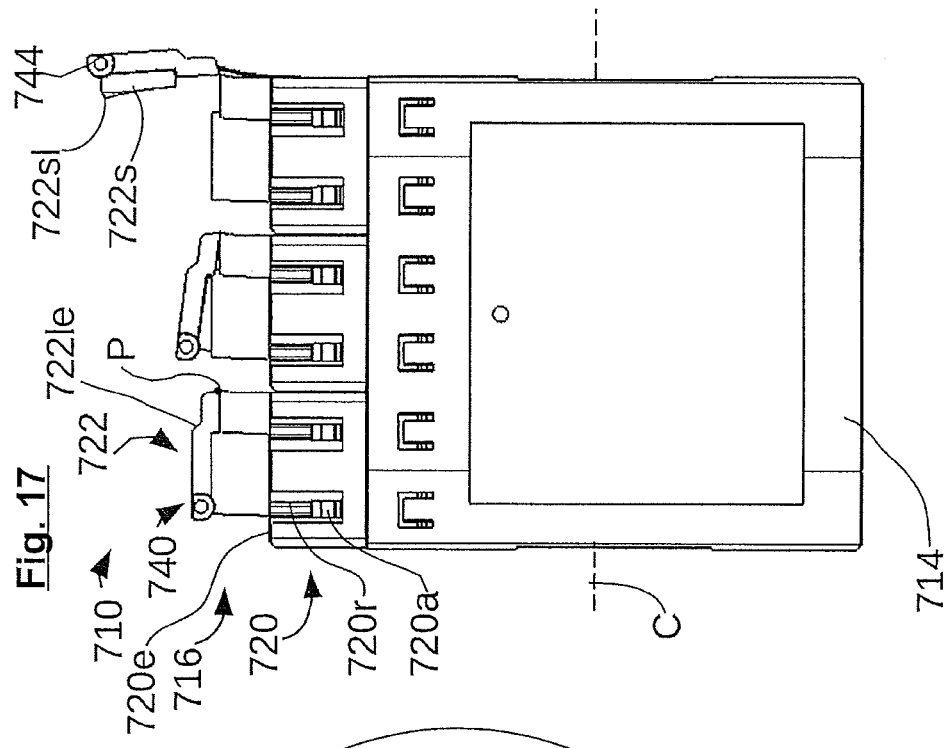
FIG. 17 shows the subject of FIGS. 16a-b in a side view.

It is noted that the same type of reagent container caps as well as the same type of reagent container support structures can be used for different reagent containers, e.g., 418 and 318 as illustrated in FIGS. 10 and 11 and illustrated in the eighth embodiment shown in FIGS. 16a, 16b and 17.

Therefore, in particular, different types of reagent containers can be mounted to one and the same reagent container support structure, e.g., in order to assemble reagent kits with a larger reagent container when a reagent is used in larger amounts for a test, and a smaller reagent container when another reagent is used in smaller amounts for a test.

Figure 6A:
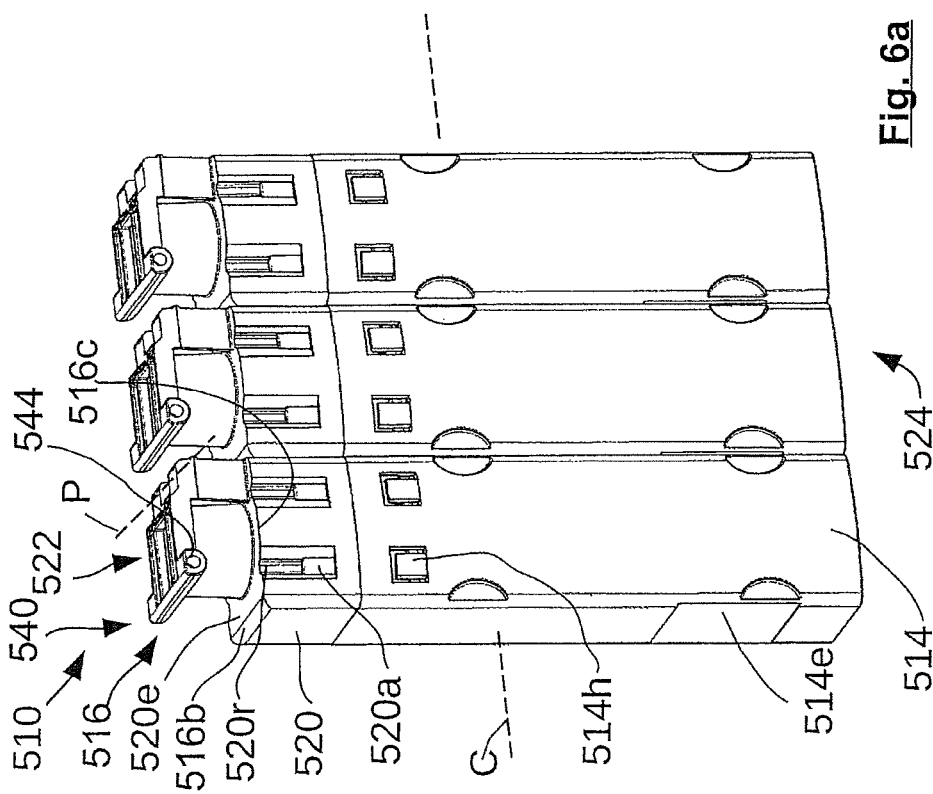

FIGS. 6a-b show a reagent container kit 510 according to a sixth embodiment of the present disclosure. In the reagent container kit 510, very similar reagent container caps 516 and reagent containers 518 are used as in the reagent container kit 410 described above. However, whereas in reagent kit 410 all reagent containers 418 are mounted to the same reagent container support structure 414, in reagent container kit 510, each reagent container 518 is mounted to a separate reagent container support structure 514.

As shown in FIG. 6a, several (e.g., three) reagent container support structures 514 can be welded to each other at portions 514w in order to form a reagent container support structure unit 524.

FIGS. 7a and 7b show a reagent container kit 610 according to a seventh embodiment of the present disclosure. In this embodiment, the reagent container support structures 614 and the central part of the reagent containers are integrally formed. The bottoms 618b of the reagent containers 618 are however separately formed and can be welded to the reagent container support structures 614.

Instead of the snap hooks 614a shown in FIG. 7b, also a snap plate as shown in FIG. 3b (226) may be provided.

With respect to FIGS. 3a-b, 6a-b and 7a-b, it is noted that the welding portions 214w, 514w and 614w can be provided at suitable positions so that also different types of reagent container support structures, e.g., 214 and 514 or 214 and 614 can be welded together in order to form a reagent container support structure unit.

FIG. 8 shows a part of the reagent container support structure 514 of FIG. 6b in more detail. FIG. 9 shows a part of the reagent container structure 414 of FIG. 5b in more detail. In both cases, the reagent container support structures 414, 514 look the same when they are rotated by 180° around a vertical middle axis indicated by M in the figures, which facilitates the orientation of the support structures 414, 514 during assembly. It will be noted that with the exception of the caps, all parts (containers and support structures) of the reagent kits shown in the figures can exhibit this twofold rotational symmetry.

Both reagent container support structures comprise a front wall 414f, 514f and a back wall 414b, 514b that are essentially planar and parallel to each other and two side walls 414s, 514s that are at least partially curved.

The curved parts of the side walls 414s, 514s may comprise an inner region A and an outer region B wherein the radius of curvature of the inner region A is larger than that of the outer region B. Typically the outer region B may again comprise an inner portion Bi and an outer portion Bo wherein the radius of curvature of the inner portion is larger than that of the outer portion. In this way, the width w of the front and back walls 414f, 414b, 514f, 514b can be made larger, providing more space for labels containing information about the content of the reagent container (FIG. 8) or the reagent container kit (FIG. 9). It is noted that the width of the regions B, Bi and Bo is exaggerated in the figures. As noted previously herein, the dimensions of some of the elements in the figures may be exaggerated relative to other elements to help improve understanding of the various embodiments of the present disclosure.

In the case of the reagent container support structure 414 for a plurality of reagent containers, central parts D of the side walls 414s can be essentially planar and parallel to each other; only the outer regions of the side walls 414s being curved.

The reagent container support structure 414 shown in FIG. 9 may be partitioned by partitioning walls 441 in three compartments 443, each adapted to accommodate a reagent container 418 (or, e.g., 318). The partitioning walls may not reach all the way down to the bottom of the reagent container support structure 414 in order not to cause any additional friction when a reagent kit standing on a surface is moved across this surface.

Vertical ribs 441r may be provided on the partitioning walls 441 for guiding the reagent containers 418 during assembly. Also other possible structures on the partitioning walls 441 are contemplated, for positioning and centering, such as, for example, transversal ribs.

The inner contour and the snap hooks 414h, 514h of the reagent container support structure 414, 514 are adapted to receive reagent containers 318, 418, 518 and reagent container caps 316, 416, 516 in two orientations (rotated by 180° around their respective vertical middle axes).

The snap hooks 514h, 414h can be disposed and formed so that they do not protrude out of the reagent container support structure 318, 514, 414 even when a reagent container 418, 518 is mounted to the reagent container support structure 418, 518 in order to prevent that the snap hooks 514h, 414h unintentionally get caught during transport or handling.

FIGS. 10 and 11, each showing a perspective sectional view of a part of FIGS. 4a and 5a, respectively, illustrate how differently formed reagent containers can be mounted to reagent container support structures and reagent container caps of the same type. Each figure shows a perspective sectional view of the upper part of the reagent kit (cap lids not shown) wherein the sectional plane extends vertically and approximately parallel to the pivot axis P.

It will be noted that the reagent kits 10, 110, 210, 310 shown in FIGS. 1a-b to 4a-b are provided with a reagent container cap as shown in FIG. 12, whereas the reagent kits 410, 510, 610 and 710 shown in FIGS. 5a-b to 7a-b, 16a-b and 17 are provided with a reagent container cap with a modified lid as shown in FIG. 13. However this is only for the sake of illustration, as all reagent kits shown can be provided with different types of cap lids. In the following, two different exemplary designs of the caps will be discussed with respect to FIGS. 12 and 13.

The reagent container cap 16 shown in FIG. 12 has a lid 22 with engagement means 40 in the form of a hook 42 formed on the upper side 22a of the lid 22 adjacent to the edge of the lid opposite to the pivot axis P. The hook 42 is bent towards the pivot axis P and comprises two hook parts 42b spaced apart in the direction parallel to the pivot axis P by a distance d. As the hook 42 is bent toward the pivot axis P it can be engaged by a stirrup-shaped engaging means of an opening/closing device provided on an analyzing apparatus.

The distance d between the hook parts 42b serves to provide space for an automatic closing device such as a roller, used when the cap 16 is closed for the first time immediately after molding; the cap material still being warm.

FIG. 13 shows a cap 416 provided with a modified lid 422. This modified lid 422 comprises two essentially bar-shaped protrusions 444 protruding from the lid 422 essentially parallel to the pivot axis P and being formed on the lid 422 adjacent to the edge of the lid 422 opposite to the pivot axis P. When transporting and handling a large amount of reagent container caps 16, 416, one might choose to use such protrusions 444 instead of the hooks 42 shown in the previous figure because these protrusions 444 are less likely to get caught with other objects than the hooks 42.

Both reagent container caps 16, 416 shown in FIGS. 12 and 13 include shoulder portions 20s, 420s formed adjacent to the edges orthogonal to the pivot axis (P) which, in a plan view on the top side of the cap 16, 416 are not covered by the lid 22, 422 in its closed position and therefore can be used to cooperate with a suitable stopping device which prevents the reagent kits from being lifted upwards when one of the lids 22, 422 is opened.

The recessed portion 420r of the cap body 420 of cap 416 differs in detail from that of cap 16 as shown in FIG. 12. In FIG. 13, the recessed portion 420, comprises an outer part 420ro and an inner part 420ri wherein the slope of the surface of the inner part 420ri with respect to side wall 420s of the cap body 420 is steeper than that of the outer part 420ro. E.g., the inner part 420ri can have an included angle of about 60° and the outer part 420ro can have an included angle of about 120°. The slope of the surface of the outer part 420ro is smaller in order to ensure a smooth engagement with a suitable positioning device (the reagent kit should not be rocked too much when the positioning device engages the recessed portion 420r). The inner part 420ri does not contact the positioning device. Therefore the slope of its surface can be larger, so that a larger snap structure 420i can be provided on the inner side of the cap body 420 below the snap openings 420a (cf., FIG. 15). Of course, a recessed portion 420r as described above and shown in FIG. 13 can also be provided on other types of caps, in particular on a cap with hook-shaped engagement means as shown in FIG. 12.

At the front side opposite the pivot axis P, the cap body 420 can comprise a rounded and/or chamfered portion 420f in order to facilitate assembly when several (in particular 3-5) reagent containers provided with caps are inserted into one and the same reagent container support structure.

Both caps 16 and 416 comprise a neck frame 16n, 416n, the vertical length of which is typically at least 6-12 mm, most typically at least 9 mm, in order to minimize evaporation when the lid 22, 422 is opened. With respect to a cap 416 with a lid 422 with T-bar shaped protrusions, this length also facilitates the engagement of the protrusions 444 by the opening/closing device.

FIG. 14 shows the cap 416 of FIG. 13 in a different perspective view. As illustrated, the lid 422 is pivotally joined to the cap body 420 by a film hinge (integral hinge) 417 which comprises two hinge parts 417a spaced apart by a distance h. A spring element 419 (over center spring) connecting the lid 422 and the cap body 420 is disposed between the two hinge parts 417a. The spring element 419 serves to bias the cap lid 422 as well to the completely or nearly closed positions shown in FIGS. 14 and 15 as to a fully opened position. Corresponding film hinges and/or spring elements can also be provided on the cap 16 of FIG. 12.

A central portion of the front side of the cap body 420 can be recessed (not shown in the figures) in order to receive the spring element 419 of the adjacent cap when the lid of this cap is opened.

The top side of the cap lid 422 is provided with several ribs 422l extending essentially perpendicular to the pivot axis P and with two ribs 422p extending essentially parallel to the pivot axis P. The ribs 422l serve to absorb forces occurring when the lid 422 is opened and closed. In particular for caps produced by injection molding, the ribs 422l also serve to absorb forces occurring when the lid 422 is closed for the first time immediately after producing the cap when the cap material is still warm.

The ribs 422p, the ribs 422l and the surface of the top side of the lid 422 surround a volume 422v that can be sealed by a suitable surface of a vacuum gripper used for handling the caps 416. The central portion 422c of the top side of the lid 422 framed by the ribs 422p, 422l can also be used for providing a marking, e.g., a bar code or dot code that can be printed or otherwise provided on this portion 422c.

The ribs 422l do not extend over the entire length of the lid 422 but start at a distance t from the film hinge 417. Furthermore, the end parts 422le of the ribs 422l next to the film hinge 417 are sloped. The distance t and the sloped end part 422l of the cap lid 422 allow the lid of another cap placed immediately adjacent behind this cap 422 to be opened even when the cap lid 422 of the cap 416 is already opened by 70°-90° (e.g., considering adjacent reagent containers in a reagent container support structure such as that shown in FIGS. 5a-b).

FIG. 15 shows a perspective sectional view of the cap 416 depicted in FIGS. 13 and 14. This view offers a clearer illustration of the snap structures 420i provided on the inner side of the cap body 420 below the snap opening 420a and sealing surfaces 422s, 420os provided on the cap lid 422 and on the cap opening 420o.

The position and form of the film hinge 417, the sealing surfaces 422s, 420os and the spring element 419 are chosen so that the nearly closed position shown in FIG. 15 is stabilized by the spring element 419 and that in this position, the lid 422 prevents or at least effectively minimizes evaporation of fluid. This applies also to the cap 16 of FIG. 12.

The reagent kit 710 according to the eighth embodiment shown in FIGS. 16a-b and 17a-b comprises at least two different types of reagent containers 718a and 718b (cf., FIG. 16b). The form of one of the reagent containers 718b corresponds to that of the reagent containers 318 shown in FIGS. 4a-b. In reagent kits used for tests involving (magnetic) beads, such a reagent container 718b can be advantageously used for storing and mixing the beads because due to its cylindrical form the interior of the reagent container 718b has no nooks and crannies in which beads or other substances could get stuck, thus facilitating the mixing.

The other two reagent containers 718a can be used for, e.g., reagents or diluents. In order to increase the amount of reagent that can be stored inside the reagent containers 718a, a bottom part 718ab of these reagent containers 718a is formed with an essentially rectangular cross-section, very similar to the reagent containers 518 shown in FIGS. 6a-b, however having mounting plates 729, 726, 727 comparable to those of the reagent containers 718b and 318 instead of the edges provided on the reagent containers 518, for mounting the reagent containers 718a to the reagent container caps 716 and to the reagent container support structure 714. Reagent or diluent containers such as the reagent containers 718a may be colored or dyed with a dark color or may be opaque in order to protect the reagents contained in the reagent container 718a from incident light.

In the alternative embodiments of FIGS. 16a-b, the reagent kit 710 may comprise multiple reagent containers of the same type, e.g., multiple reagent containers of the type 718a (very similar to the concept with multiple reagent containers 418 shown in FIG. 5b) or multiple reagent containers of the type 718b (very similar to the concept with multiple reagent containers 318 shown in FIG. 4b).

The reagent containers 718a, 718b as well as the other reagent containers shown in the figures can be manufactured by, e.g., injection blow molding, i.e., in a two-stage process wherein first an upper part 718at, 718bt comprising the topside opening 718o and the mounting plates 726, 727, 729 is formed by injection molding, permitting very tight process tolerances. Afterwards, the bottom part 718ab, 718bb of the reagent containers is blow molded. In alternative embodiments, the complete reagent containers 718a, 718b as well as the other reagent containers shown in the figures can be manufactured by classical injection molding techniques.

The reagent caps 716 of the reagent kit 710 correspond essentially to the reagent caps 416 shown in FIGS. 5a-b, 14 and 15. However, the sealing surface 722s of the cap lid 722 is formed slightly asymmetrical having a sealing lip 722sl in a region of the sealing surface 722s opposite the pivot axis P that reaches down further than the sealing surface 722s in a region near the pivot axis P, in order to ensure that no gap forms between the cap lid 722 and the neck frame 716n in the nearly closed position (soft-close position) so that evaporation is minimized.

In the side view of FIG. 17, for illustrative purposes, the cap lids 722 of the caps 720 provided on the left reagent container 718a, the middle reagent container 718a and the right reagent container 718b are in the fully closed position, in the nearly closed position (soft close position) and in the fully opened position, respectively.

During transport, the cap lids of all caps provided on a reagent kit are typically in the fully closed position, whereas during use in an analyzing apparatus it can be typical that the cap lids are in the nearly closed position (soft close position) as long as they are not used in order to reduce the forces necessary for opening and closing the reagent containers.

Figure 18:
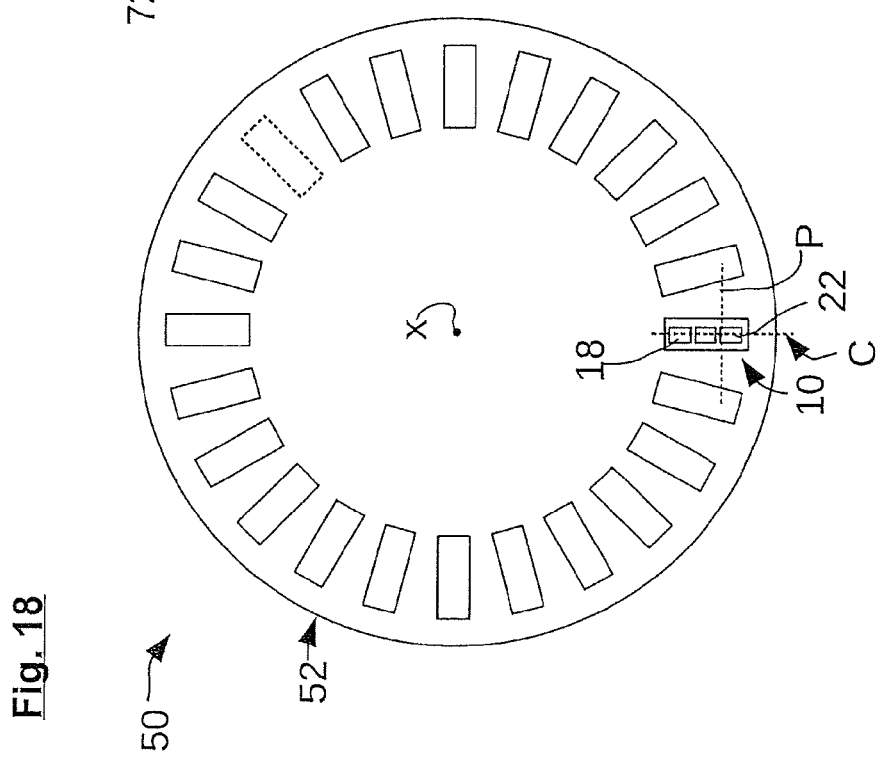
FIG. 18 shows a plan view on the top side of an analyzing apparatus provided with reagent kits according to one or more embodiments of the present disclosure.

The reagent kits 10-710 described herein can be used in an analyzing apparatus 50, typical parts of which are shown in FIG. 18. Such an analyzing apparatus 50 can comprise a turntable 52 on which a plurality of reagent kits 10 according to the present disclosure are arranged.

It is noted that FIG. 18 is a highly simplified and schematic illustration of parts of the analyzing apparatus 50. For reasons of clarity, only one reagent kit 10 is provided with a reference sign and only on this reagent kit, the placement of the lids 22 of the reagent container caps included in the reagent kit is indicated in the figure.

The turntable 52 shown in FIG. 18 is rotatable around the axis X, which is essentially orthogonal to the drawing plane.

The reagent kits 10 placed on different positions on the turntable 52 can comprise different reagent containers with different reagents for different tests to be conducted on, e.g., a liquid sample. When a specific test is to be conducted, the corresponding reagent kit 10 placed on the turntable 52 can be rotated to a predetermined position. There the reagent container cap of the desired reagent container can be opened by an automatic opening/closing device (not shown in the figure) and afterwards a quantity of the reagent can be taken from the container 18 by a (not shown) pipetting device.

As the reagent kits 10 are arranged radially on the turntable 52, in order to place a large number of reagent kits 10 on the turntable 52 the reagent kits 10 have to be as small as possible in the circumferential direction. This can be achieved by reagent kits according to various embodiments of the disclosure because the dimension of those reagent kits 10 in the circumferential direction of the turntable 52, i.e., their width, is mainly determined by the diameter of the reagent containers 18.

Whether the reagent kits are oriented so that the pivot axes P are disposed on the radially inner side (as indicated in the figure) or on the radially outer side of the turntable depends mainly on the opening/closing device used.

It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present invention.

It is also noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modifications and variations come within the scope of the appended claims and their equivalents.

What is claimed is:

1. A reagent kit adapted for use in an analyzing apparatus having a pipetting device and a reagent container opening/closing device, the reagent kit comprising:

a plurality of reagent containers, each with a top-side opening;
a common reagent container support structure, or a plurality of reagent container support structures, in the latter case each of the reagent container support structures being associated to one of the reagent containers, wherein each reagent container is mountable or provided on the common or the associated reagent container support structure; and
a plurality of reagent container caps, each of which is associated to one of the reagent containers, each reagent container cap being mountable or provided on the common or the associated reagent container support structure, wherein, in a plan view on the top side of the reagent kit, each reagent container cap is formed essentially rectangular, having two shorter edges and two longer edges, and wherein each reagent container cap comprises:
a cap body,
a lid hinged to the cap body so as to be pivotable around a pivot axis at least between a closed position and an opened position, wherein the pivot axis is essentially parallel to the shorter edges of the reagent container cap, and
engagement means which are adapted to cooperate with the reagent container opening/closing device in order to pivot the lid between the closed position and the opened position,
the reagent containers and the associated reagent container caps are arranged in a row along a connecting line in such a manner that the pivot axes of the reagent container caps are orthogonal to the connecting line, and that, for at least one of the reagent containers, when the at least one reagent container and the associated reagent container cap are provided on the common or the associated reagent container support structure, and when the lid of the associated reagent container cap is in the closed position, in a plan view on the top side of the reagent kit, an end portion of the cap body opposite to the pivot axis is not covered by the lid.

2. The reagent kit according to claim 1, wherein for at least one of the reagent containers, the common or the associated reagent container support structure and the at least one reagent container are separately formed, and the at least one reagent container is adapted to be snapped and/or welded to the common or the associated reagent container support structure.

3. The reagent kit according to claim 1, wherein for at least one of the reagent containers, the common or the associated reagent container support structure and the at least one reagent container are integrally formed.

4. The reagent kit according to claim 2, wherein the common or the associated reagent container support structure and the reagent container cap associated to the at least one reagent container are integrally formed.

5. The reagent kit according to claim 1, wherein for at least one of the reagent containers, the common or the associated reagent container support structure and the associated reagent container cap are separately formed, and the associated reagent container cap is adapted to be snapped on the common or the associated reagent container support structure, or on the at least one reagent container.

6. The reagent kit according to claim 1, wherein the reagent containers and the associated reagent container caps are mounted or mountable to one and the same common reagent container support structure.

7. The reagent kit according to claim 1 further comprising a plurality of reagent container support structures, each reagent container support structure associated to one of the reagent containers, wherein the reagent container support structures are arranged in a row along the connecting line and adjacent reagent container support structures are fixed to each other, forming a reagent container support structure unit.

8. The reagent kit according to claim 7, wherein adjacent reagent container support structures are fixed to each other by ultrasonic welding.

9. The reagent kit according to claim 5, wherein for at least one of the reagent containers, the cap body of the associated reagent container cap comprises a snap opening and the common or the associated reagent container support structure or the at least one reagent container comprises a snap hook or snap structure adapted to snap into the snap opening when the associated reagent container cap is mounted to the common or the associated reagent container support structure or to the at least one reagent container.

10. The reagent kit according to claim 9, wherein the surface of the cap body of the reagent container cap associated to the at least one reagent container has a recessed portion immediately above the snap opening.

11. The reagent kit according to claim 10, wherein the recessed portion of the surface of the cap body of the reagent container cap associated to the at least one reagent container is adapted to cooperate with a positioning device of the analyzing apparatus.

12. The reagent kit according to claim 6, wherein the common reagent container support structure or the reagent container support structure unit has at least one tapered end portion along the connecting line.

13. The reagent kit according to claim 1, wherein for at least one of the reagent containers, an upper surface of the cap body of the associated reagent container cap comprises two shoulder portions formed adjacent to the edges orthogonal to the pivot axis which, in a plan view on the top side of the reagent kit, are not covered by the lid of the associated reagent container cap in its closed position.

14. The reagent kit according to claim 1, wherein for at least one of the reagent containers, the engagement means of the associated reagent container cap comprise a hook formed on the upper side of the lid adjacent to the edge of the lid opposite to the pivot axis, wherein the hook is bent towards the pivot axis.

15. The reagent kit according to claim 1, wherein for at least one of the reagent containers, the engagement means of the associated reagent container cap comprise two essentially bar-shaped protrusions protruding from the lid essentially parallel to the pivot axis and being formed on the lid adjacent to the edge of the lid opposite to the pivot axis.

16. An analyzing apparatus comprising a pipetting device, a reagent container opening/closing device and a turntable adapted to receive a plurality of reagent kits, wherein said apparatus comprises a plurality of reagent kits according to claim 1, and wherein said reagent kits are arranged on the turntable so that the pivot axes of the reagent container caps are tangential to a circumferential direction of the turntable.

* * * * *